US006483013B1

(12) United States Patent
Reynaerts et al.

(10) Patent No.: US 6,483,013 B1
(45) Date of Patent: Nov. 19, 2002

(54) METHOD FOR AGROBACTERIUM MEDIATED TRANSFORMATION OF COTTON

(75) Inventors: Arlette Reynaerts, Brongen (BE); Anne De Sonville, Merelbeke (BE)

(73) Assignee: Bayer BioScience N.V. (BE)

( * ) Notice: Subject to any disclaimer, the term of this patent is extended or adjusted under 35 U.S.C. 154(b) by 0 days.

(21) Appl. No.: 09/573,555

(22) Filed: May 19, 2000

Related U.S. Application Data
(60) Provisional application No. 60/219,317, filed on May 19, 1999.

(51) Int. Cl.[7] ............... C12N 15/84; C12N 5/04; A01H 1/00; A01H 5/00; A01H 5/10

(52) U.S. Cl. ............ 800/294; 800/278; 800/260; 800/314; 435/469; 435/419; 435/427; 435/430; 435/430.1

(58) Field of Search ................ 800/278, 294, 800/314, 260; 435/469, 419, 427, 430.1, 430

(56) References Cited

U.S. PATENT DOCUMENTS

| | | | |
|---|---|---|---|
| 4,954,442 A | 9/1990 | Gelvin et al. | |
| 5,004,863 A | 4/1991 | Umbeck | |
| 5,159,135 A | 10/1992 | Umbeck | |
| 5,164,310 A | 11/1992 | Smith et al. | |
| 5,244,802 A | 9/1993 | Rangan | |
| 5,583,036 A | 12/1996 | Rangan et al. | |
| 5,846,797 A | * 12/1998 | Strickland | 435/172.3 |

FOREIGN PATENT DOCUMENTS

| | | |
|---|---|---|
| EP | 0270355 | 2/1987 |
| EP | 0242236 | 10/1987 |
| EP | 0242246 | 10/1987 |
| EP | 0531506 | 12/1998 |
| WO | 89/05344 | 6/1989 |
| WO | 89/12102 | 12/1989 |
| WO | 92/15675 | 9/1992 |
| WO | 97/12512 | 4/1997 |
| WO | 97/43430 | 11/1997 |
| WO | 98/15622 | 4/1998 |
| WO | 98/31822 | 7/1998 |
| WO | 98/37212 | 8/1998 |
| WO | 00/04611 | 5/2000 |

OTHER PUBLICATIONS

Still, S. M. et al., "Phytotoxic Effects of Several Bark Extracts on Mung Bean and Cucumber Growth." 1976, J. Amer. Soc. Hort. Sci., vol. 101, pp. 34–37.*
Chair, H. et al., "Agrobacterium Mediated Transformation of Sri Sumrong 60, a Thai Cotton Variety." 1997, Kasetsart J., vol. 33, pp. 149–156.*
Otani, M. et al., " Transgenic Plant Production from Embryogenic Callus of Sweet Potato (Ipomoea batatas (L.) Lam.) Using Agrobacterium tumefaciens." 1998, Plant Biotechnology, vol. 15, pp. 11–16.*
Sheikholeslam, S. N. and Weeks, D. P., "Acetosyringone promotes high efficiency transformation of Arabidopsis thaliana explants by Agrobacterium tumefaciens." 1987, Plant Molecular Biology, vol. 8, pp. 291–298.*
Ashby et al., *Ti Plasmid–Specified Chemotaxis of Agrobacterium tumefaciens C58C[1] toward vir–Inducing Phenolic Compounds and Soluble Factors from Monocotyledonous and Dicotyledonous Plants*, (1988, J. Bacteriol. 170: 4181–4187).
Stachel et al., *Identification of the signal molecules produced by wounded plant cells that activate4 T–DNA transfer in Agrobacterium tumefaciens*, (1985 Nature 318: 624–629).
Bolten et al., *Plant Phenolic Compounds Induce Expression of the Agrobacterium tumefaciens Loci Needed for Virulence*, (1986, Science 232: 983–985).
Firoozabady, et al., *Transformation of cotton (Gossypium hisutum L.) By Agrobacterium tumefaciens and regeneration of transgenic plants*, (1987, Plant Molecular Biology 10: 105–116).
Unbeck, et al., *Genetically Transformed Cotton (Gossypium Hirsutum L.) Plants*, (1987, Bio/Technology 5:263–266).
Finer and McMullen, *Transformation of cotton ( Gossypium hisutum L.) Via particle bombardment*, (1990, Plant Cell Reports, i:586–589).
McCabe and Martinell, *Transformation of Elite Cotton Cultivars via Particle Bombardment of Meristems*, (1993, Bio/Technology 11:596–598).
Hansen et al., *Constitutive expression of the virulence genes improves the efficiency of plant transformation by Agrobacterium*, (1994, Proc. Nat'l Acad. Sci. 91:7603–7607).
Veluthambi et al., *Opines Stimulate Induction of the vir Genes of the Agrobacterium tumefaciens Ti Plasmid*, (1989, Journal of Bacteriology 171: 3696–3703).
Chen & Winans, *Controlled Expression of the Transcriptional Activator Gene virG in Agrobacterium tumefaciens by Using the Escherichia coli lac Promoter*, (1991, J. Bacteriol. 173: 1139–1144).
Scheeren–Groot et al., *Mutational Analysis of the Transcriptional Activator VirG of Agrobacterium tumefaciens*, (1994, J. Bacteriol. 176: 6418–6246).
Vernade et al., *Glycine Betaine Allows Enhanced Induction of the Agrobacterium tumefaciens vir Genes by Acetosyringone at Low pH*, (1988, J. of Bacteriol 170: 5822–5829).

(List continued on next page.)

Primary Examiner—David T. Fox
Assistant Examiner—Anne Kubelik
(74) Attorney, Agent, or Firm—Hunton & Williams

(57) ABSTRACT

This invention relates to improved methods for the production of transgenic cotton plants, comprising cocultivating Agrobacterium cells comprising a DNA fragment of interest operably linked to at least one T–DNA border with cotton embryogenic callus in the presence of a plant phenolic compound.

10 Claims, No Drawings

OTHER PUBLICATIONS

Murray et al., *Transgenic Cotton*, (1993), Transgenic Plants, vol. 2, pp. 153–168.

Owens et al., *Transformation of Soybean Cells Using Mixed Strains of Agrobacterium tumefaciens and Phenolic Compounds*, (1988), Plant Physiology, vol. 88, pp. 570–573.

Hoshino et al., *Production of Transgenic Grapevine (Vitis vinifera L. cv. Koshusa"jaku) Plants by Co–cultivation of Embryogenic Calli with Agrobacterium tumefaciens and Selecting Secondary Empryos*, (1988, Plant Biotechnology, 15(I). 29–33).

* cited by examiner

US 6,483,013 B1

METHOD FOR AGROBACTERIUM MEDIATED TRANSFORMATION OF COTTON

PRIORITY OF INVENTION

This application claims priority under 35 USC §119(e) from U.S. Provisional Application Serial No. 60/219,317 filed May 19, 1999, the disclosure of which is hereby incorporated by reference. The provisional application was filed as a nonprovisional application under 37 C.F.R. §1.53 (b) on May 19, 1999, and converted to a provisional application on May 19, 2000, by virtue of a Petition for conversion of application Ser. No. 09/314,449 to a Provisional Application Under 37 C.F.R. §1.53(c)(2) filed concurrently herewith.

BACKGROUND OF THE INVENTION (i) Field of the invention

This invention relates to the field of plant transformation, particularly to an improved method for Agrobacterium mediated transformation of cotton.

(ii) Description of the Related Art

Cotton is an important crop, grown primarily for its lint, which provides much of the high quality fiber for the textile industry. Cotton seed is also a valuable commodity, as it provides a source for oil, meal and seed hulls.

About 90 % of cotton grown worldwide is *Gossypium hirsutum* L., whereas *Gossypium barbadense* accounts for about 8%.

Improvement of various traits such as resistance to pests, stress or disease, fiber quality, reduced gossypol content, has been obtained by conventional breeding techniques, and further improvement of these and other traits can be achieved using molecular and genetic techniques.

Several methods are available for the transformation of cotton including Agrobacterium mediated transformation of cotton explants, such as isolated cotyledons, isolated hypocotyls and isolated hypocotyl transition zones, as well as direct gene transfer by microprojectile bombardment of meristimatic cotton tissues.

Firoozabady et al. (1987, Plant Molecular Biology 10:105–116) described transformation of cotton cotyledon tissues by *Agrobacterium tumefaciens* and regeneration of transgenic plants.

Umbeck et al (1987, Bio/Technology 5: 263–266) reported results on cotton transformation via Agrobacterium using hypocotyls as explants.

PCT publication ("WO") 89/05344, ("U.S.") U.S. Pat. Nos. 5,244,802 and 5,583,036 provide methods for regeneration of cotton by tissue and suspension culture starting with explants which are the hypocotyl, cotyledon or immature embryos. Also taught is a method to transform cotton and improve cotton by selective growth.

WO 89/12102 and U.S. Pat. No. 5,164,310 relate to a novel method for transforming and rapidly regenerating plant tissue. The method employs target tissues which are the shoot apices, thereby expanding the species range for transformation and reducing the risk of somaclonal variation.

WO 98/15622 provides a method for the in vitro regeneration of fertile Gossypium plants in which cells from the transition region tissue of seedlings is excised and cultured. A method for the production of transgenic Gossypium plants capable of transmitting a foreign gene to progeny is also described in which cells derived from the transition region tissue of seedlings are targeted for transformation.

WO 97/12512 provides a method for regenerating cotton plants from explant tissue which allows the generation of embryogenic callus from a cotton tissue explant, such as a hypocotyl, which is not cultivated on callus initiation media having exogenous plant hormones. The method can be utilized in the Agrobacterium-mediated transformation of cotton plants.

U.S. Pat. Nos. 5,004,863 and 5,159,135 and European patent publication "EP"0 270 355 all disclose a method to achieve genetic transformation of cotton plants and lines, by subjecting immature cotton tissues such as hypocotyl segments in vitro to Agrobacterium mediated genetic transformation.

WO 97/43430 relates to a versatile method of rapidly regenerating cotton plants from explants of apical and/or nodal meristematic tissues which can be coupled with well known methods of transformation such as Agrobacterium-mediated transformation for the rapid production of genetically-engineered cotton varieties of agronomic importance.

WO 92/15675 and EP 0 531 506 describe a method for the particle-mediated transformation of cotton permitting the direct genetic engineering of elite cotton lines without the need for tissue culture or callus proliferation, involving excision of the embryonic axes from germinating seeds and blasting particles carrying foreign genes into the embryonic axes.

Finer and Mc Mullen (1990, Plant Cell Reports, 8: 586–589) described transformation of cotton via particle bombardment of embryogenic suspension cultures.

McCabe and Martinell, (1993, Bio/Technology 11: 596–598) have described transformation of elite cotton cultivars via particle bombardment of cotton meristematic tissue from excised embryonic axes.

Hansen et al (1994, Proc. Natl. Acad. Sci. 91: 7603–7607) have described an Agrobacterium strain comprising a constitutive virg mutant (virGN54D) leading to enhanced transformation efficiencies of isolated cotton cotyledons.

Veluthambi et al. (1989, Journal of Bacteriology 171: 3696–3703) described a markedly increased transformation of cotton shoot tips by the simultaneous addition of acetosyringone and nopaline at the time of infection.

The cotton Agrobacterium-mediated transformation methods characterizing the art to date suffer from the major drawback, as indicated in Murray et al. (1993, in Transgenic Plants Vol 2, Academic Press Inc. p153–168) that the time required to regenerate a transgenic plant from an explant which has been co-cultivated with Agrobacterium cells is extremely long.

Moreover, an additional problem arises from the fact that all described Agrobacterium mediated transformation methods of cotton require the generation of embryogenic callus from the explant containing the transformed cells, as an intermediate step in the regeneration of transgenic cotton plants. Since not all transformed cells of the explant necessarily are competent for the initiation of embryogenic callus, a loss of regeneration of a number of potentially transgenic cells, which consequently results in a low transformation efficiency, is observed with these methods. An increase in starting numbers of putative transformed cotton explants to compensate for this loss, results in an huge increase of the amount of labor to be invested in obtaining regenerated transgenic cotton plants.

WO 89/05344 has suggested in general terms that embryogenic callus may be used as appropriate starting material for Agrobacterium mediated transformation of cotton callus. Nevertheless, during the past decade no reports were made of successful production of transgenic cotton plants using co-cultivation of embryogenic callus with Agrobacterium.

To some extent, this problem has been alleviated by techniques in microprojectile bombardment of meristematic tissue which result in a larger number of transgenic cotton lines. Nonetheless, the generation of germline transformed cotton plants, which are capable of passing on the transgene to their progeny, is infrequent.

The art is thus deficient in providing an efficient method, both in terms of required time and transformation efficiency, for the generation of transgenic cotton plants which are capable of transferring the foreign incorporated DNA to their progeny plants.

SUMMARY AND OBJECTS OF THE INVENTION

In view of the foregoing shortcomings associated with prior art cotton transformation processes as well as other disadvantages not specifically mentioned above, it should be apparent that there still exists a need in the art for a method of transforming cotton which achieves the heretofore elusive combination of a high transformation efficiency in a relatively short period of time. It is, therefore, a primary objective of the present invention to fulfill that need by providing a method for producing a transgenic cotton plant, preferably a fertile transgenic plant, by Agrobacterium-mediated transformation, comprising co-cultivating Agrobacterium cells comprising a DNA fragment of interest operably linked to at least one T-DNA border with cotton embryogenic callus in the presence of a plant phenolic compound.

It is another object of the present invention to provide a process for producing a transgenic cotton plant which eliminates the step of generating embryogenic callus from a cotton explant comprising the transformed cells, thereby both reducing the potential loss of transformed cotton lines from transformed plant cells which are not capable of generating embryogenic callus and enhancing transformation frequencies.

In a first aspect, the present invention relates to a method for producing a transgenic cotton plant comprising incubation of Agrobacterium cells comprising a DNA fragment of interest operably linked to at least one T-DNA border, with a plant phenolic compound prior to or during the co-cultivation of cotton embryogenic callus with the Agrobacterium cells.

In another aspect, the present invention relates to a method for producing a transgenic cotton plant, comprising:
  i) co-cultivating cotton embryogenic callus, preferably derived from a hypocotyl of a cotton seedling, with Agrobacterium cells, the Agrobacterium cells comprising a DNA fragment of interest operably linked to at least one T-DNA border, in the presence of a plant phenolic compound, preferably selected from the group consisting of acetosyringone, α-hydroxy-acetosyringone, sinapinic acid, syringic acid, ferulic acid, catechol, p-hydroxybenzoic acid, β-resorcylic acid, protocatechuic acid, pyrrogallic acid, gallic acid and vanillin, preferably present in a concentration range from about 50 $\mu$M to about 400 $\mu$M, for a time sufficient to generate embryogenic callus comprising a transformed cotton cell, preferably for about 3 to 4 days;
  ii) regenerating a transgenic cotton plant from the transformed cell; and optionally
  iii) crossing said transgenic cotton plant with another cotton plant In another aspect, the present invention relates to the use of a plant phenolic compound, preferably acetosyringone, for Agrobacterium mediated transformation of cotton embryogenic callus.

DETAILED DESCRIPTION OF PREFERRED EMBODIMENTS

The inventors have developed an improved and accelerated Agrobacterium mediated transformation method for the production of transgenic cotton plants, comprising the use of a plant phenolic compound, such as acetosyringone, during Agrobacterium mediated transformation of cotton embryogenic callus, preferably during the co-cultivation stage of cotton embryogenic callus with Agrobacterium cells. This method on average leads to a time reduction in the period starting from co-cultivation towards the time point at which the transgenic cotton plant is sufficiently developed to be transferred to soil, preferably under greenhouse conditions, of at least about 2 to 3 months.

Since the improved method of this invention comprises the use of embryogenic callus as starting tissue for the transformation, the step of generating embryogenic callus from the cotton explant comprising the transformed cells, is eliminated. Consequently, the potential loss of transformed cotton lines from transformed plant cells which are not capable to generate embryogenic callus is reduced, and transformation frequencies are enhanced.

Moreover, embryogenic callus, once initiated, can be maintained relatively easily (as long as somaclonal variation does not interfere with phenotype of regenerated plants) thus facilitating the management of the supply of starting material for transformation experiments.

The inventors have surprisingly found that Agrobacterium mediated transformation of cotton embryogenic callus, necessitated the addition of a plant phenolic compound, such as but not limited to acetosyringone, preferably at the co-cultivation stage. Nowhere in the prior art has it been suggested that the inclusion of such a plant phenolic compound, of all possible variables, would lead to successful Agrobacterium mediated transformation of cotton embryogenic callus.

In one embodiment, the invention relates to the use of a plant phenolic compound during the Agrobacterium-mediated transformation of cotton embryogenic callus.

"Plant phenolic compounds" or "plant phenolics" suitable for the invention are those substituted phenolic molecules which are capable of inducing a positive chemotactic response, particularly those which are capable of inducing increased vir gene expression in a Ti-plasmid containing Agrobacterium sp., particularly a Ti-plasmid containing *Agrobacterium tumefaciens*. Methods for measuring chemotactic response towards plant phenolic compounds have been described by Ashby et al. (1988, J. Bacteriol. 170: 4181–4187) and methods to measure induction of vir gene expression are also well known (Stachel et al., 1985 Nature 318: 624–629; Bolton et al. 1986, Science 232: 983–985).

Preferred plant phenolic compounds are those found in wound exudates of plant cells. One of the best known plant phenolic compounds is acetosyringone, which is present in a number of wounded and intact cells of various plants, albeit it in different concentrations. However, acetosyringone (3,5-dimethoxy-4-hydroxyacetophenone) is not the only plant phenolic which can induce the expression of vir genes. Other examples are α-hydroxy-acetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde), and these phenolic compounds are known or expected to be able to replace acetosyringone with similar results. As used herein, the mentioned molecules are also referred to as plant phenolic compounds.

Plant phenolic compounds can be used either alone or in combination with other plant phenolics. Certain compounds, such as osmoprotectants (e.g. L-proline or betaine), phytohormes, (inter alia NAA), opines, or sugars, are expected to act synergistically when added in combination with plant phenolic compounds.

In a preferred embodiment, the invention relates to a method for transforming a cotton plant, i.e. producing a transgenic cotton plant by introduction of a DNA fragment of interest into the genome of the cells of a cotton plant, wherein the method comprises:

a) co-cultivating cotton embryogenic callus with Agrobacterium cells, the Agrobacterium cells comprising a DNA fragment of interest operably linked to at least one T-DNA border, in the presence of a plant phenolic compound, for a time sufficient to generate embryogenic callus comprising a transformed cotton cell; and b) regenerating a transgenic cotton plant from said transformed cell.

The methods provided by the invention employ cotton embryogenic callus as starting material for the co-cultivation with the Agrobacterium cells. As used herein "cotton embryogenic callus" or "embryogenic callus derived from a cotton explants" refers to compact or solid callus tissue, cultivated on solid media, derived from a cotton explant, which can be regenerated into an intact cotton plant through somatic embryogenesis. This definition of embryogenic cotton callus does not include embryogenic suspension cells, cultured in liquid medium.

Methods to induce embryogenic callus from a cotton explant have been disclosed in the art, e.g. in WO 97/12512.

It will be clear for the skilled artisan, that the source of the cotton explant from which embryogenic callus has been derived is only of limited importance for the method of the current invention. Embryogenic callus may be derived from any suitable cotton explant such as but not limited to hypocotyls, cotyledons, immature or mature embryos etc.

Preferably, the cotton embryogenic callus used in the transformation methods described herein, was obtained by incubation of cotton hypocotyl explants on hormone free callus induction medium as described in WO 97/12512.

"Co-cultivation" is used herein to indicate the process of contacting between the embryogenic cotton callus and the Agrobacterium cells, prior to the addition of bacteriostatic or bacteriocidal compounds to inhibit or eliminate the Agrobacteria. The "co-cultivation stage" of an Agrobacterium mediated transformation method thus refers to the time period between the initial contacting of the Agrobacteria with the plant tissue, until the time point where a bacteriostatic or bacteriocidal compound is added to the medium with the intention to remove or inhibit the Agrobacterium strains comprising the DNA fragment of interest.

"A DNA fragment of interest" is used herein to describe any DNA fragment which one would like to introduce into the genome of cells of a cotton plant, irrespective of whether it encodes a protein or polypeptide, RNA or not. Indeed, a DNA fragment may be introduced mainly for tagging purposes. The only prerequisite for the DNA fragment of interest is that it should be "operably linked to at least one T-DNA border."

As used herein, "a T-DNA border" encompasses a DNA fragment comprising an about 25 nucleotide long sequence capable of being recognized by the virulence gene products of an Agrobacterium strain, preferably an A. tumefaciens or A. rhizogenes strain, and sufficient for transfer of the operably linked DNA to eukaryotic cells, preferably plant cells, particularly sufficient for transfer and integration of the operably linked DNA into the genome of a eukaryotic cell, preferably a plant cell. It is clear that this definition encompasses all naturally occurring T-DNA borders from wild-type plasmids, as well as any functional derivative thereof, including chemically synthesized T-DNA borders.

Preferably, the DNA of interest is located between two T-DNA borders, preferably on T-DNA vector capable of forming a hybrid Ti-plasmid by single cross-over through a fragment of DNA homology between the T-DNA vector and the helper Ti-plasmid.

The use of a plant phenolic compound according to the invention increases the transformation efficiency of Agrobacterium mediated DNA transformation of cotton embryogenic callus, and it is expected that this effect is independent of the chromosomal background of the Agrobacterium host, the type of Ti-plasmid, helper-plasmid or T-DNA vector used.

Particularly preferred bacterial chromosomal backgrounds are provided by A. tumefaciens C58C1 (Van Larebeke et al., 1974, Nature 252: 169–170), A136 (Watson et al., 1975, J. Bacteriol 123: 255–264) or LBA401 1( Klapwijk et al., 1980, J. Bacteriol 141, 128–136).

In a preferred embodiment, the Agrobacterium strain used to transform the plant tissue precultured with the plant phenolic compound contains a LL-succinamopine type Ti-plasmid, preferably disarmed, such as pEHA101.

The method of the invention can also be used in combination with particular Agrobacterium strains, to further increase the transformation efficiency, such as Agrobacterium strains wherein the vir gene expression and/or induction thereof is altered due to the presence of mutant or chimeric virA or virG genes (e.g. Hansen et al., 1994, supra; Chen and Winans, 1991, J. Bacteriol. 173: 1139–1144; Scheeren-Groot et al., 1994, J. Bacteriol. 176:6418–6246).

In another embodiment, Agrobacterium strains comprising an extra virG gene copies, particularly the so-called super virG gene derived from pTiBo542, preferably linked to a multiple-copy plasmid, can be used to further increase the transformation efficiency.

The concentration of the plant phenolic compound in the co-cultivation medium is also believed to have an effect on the transformation efficiency. However, within certain concentration ranges, the effect is minimal. The optimal concentration range of plant phenolic compounds in the co-cultivation medium may vary depending on the species or variety from which the cotton embryogenic callus is derived, but it is expected that about 100 μM is a suitable concentration for many purposes. The optimal concentration may also depend on the nature of the specific plant phenolic compound used, particularly on its cell-division promoting strength.

It was found for instance that the optimal concentration for acetosyringone is approximately 100 μM, but concentrations as low as approximately 25 µM can be used to obtain a good effect on transformation efficiency. Likewise, it is expected that higher concentrations up to approximately 400 µM will yield similar effects.

Comparable concentrations apply to other plant phenolic compounds, and optimal concentrations can be established easily by experimentation in accordance with this invention.

Typical co-cultivation times to generate a cotton embryogenic callus comprising transformed cells, are about 3 to about 4 days, but it is expected that a co-cultivation time of one day may be sufficient to generate at least some transformed cells. Further, it is expected that co-cultivation times should not exceed about 7 days.

It is clear for the skilled artisan that in addition to inclusion of a plant phenolic compound during co-cultivation of cotton embryogenic callus with Agrobacterium cells, the used Agrobacterium cells may also be preinduced by incubation with a plant phenolic compound for a time sufficient to induce the virulence genes of the Agrobacterium cells.

Moreover, it is expected that preinduction of Agrobacterium cells with a plant phenolic compound for a time sufficient to induce the virulence genes of the Agrobacterium cells, might obviate the requirement for inclusion of a plant phenolic compound during the co-cultivation stage.

Thus, in another preferred embodiment, the invention relates to a method for transforming a cotton plant, i.e., producing a transgenic cotton plant by introduction of a DNA fragment of interest into the genome of the cells of a cotton plant, wherein the method comprises:
 a) incubating an Agrobacterium cell culture comprising a DNA fragment of interest operably linked to at least one T-DNA border, with a plant phenolic compound, for a time sufficient to induce virulence genes of the Agrobacterium cells;
 b) co-cultivating embryogenic callus derived from a cotton explant with the Agrobacterium cells incubated with the plant phenolic compound, so as to generate embryogenic callus comprising a transformed cotton cell; and
 c) regenerating a transgenic cotton plant from the transformed cell.

Methods to preinduce the virulence genes of Agrobacterium cells by incubation with a plant phenolic compounds, as well as methods to determine whether the virulence genes of an Agrobacterium strain are induced, are available in the art, e.g. as described by Stachel et al., 1985 or Bolton et al. 1986.

Optimized methods for induction of Agrobacteria with plant phenolic compounds, particularly acetosyringone, have been described e.g. by Vernade et al., (1988, J. of Bacteriology 170: 5822–5829) incorporated herein by reference.

The time of incubation of Agrobacterial cells with a plant phenolic compound sufficient to induce the virulence genes may range from a few hours to about two days prior to co-cultivation, but typically about one day incubation prior to co-cultivation will be sufficient. Likewise, concentrations of the plant phenolic compound may range from about 50 µM to about 400 µM, but typically about 100 µM will be a preferred concentration for the plant phenolic compound.

After co-cultivation, the cotton embryogenic callus is preferably submitted to a selection regime to separate transformed cells from untransformed cells or to at least enrich for transformed cells.

To this end, the foreign DNA used in the method of this invention preferably also comprises a marker gene, the expression of which allows the separation of transformed cells from non-transformed cells. Such a marker gene generally encodes a protein which allows one to phenotypically distinguish transformed cells from untransformed cells. In the case of a selectable marker gene, resistance to an antibiotic or other chemical compound that is normally toxic for the cells is generally provided to the cell by expression of that marker gene. In plants the selectable marker gene may thus also encode a protein that confers resistance to a herbicide, such as a herbicide comprising a glutamine synthetase inhibitor (e.g. phosphinothricin) as an active ingredient. An example of such genes are genes encoding phosphinothricin acetyl transferase such as the sfr or sfrv genes (EP 0 242 236; EP 0 242 246; De Block et al., 1987, EMBO J. 6: 2513–2518). However, it can also be that the distinguishable phenotype cannot be selected for, as is the case for marker genes normally referred to a screenable marker genes, including but not limited to, green fluorescent proteins (GFP) or β-glucuronidases (GUS) or β-lactamases well known in the art.

Moreover, using methods such as PCR-based DNA amplification methods, any DNA sequence, including part of the sequence of the DNA of interest, may be used as a tag for verification of the presence of the DNA fragment of interest.

Selection of transformed embryogenic callus cells is preferably performed on solid media, but can also be supplemented or replaced by a selection phase in liquid medium.

It goes without saying that during the selection and, if required, the regeneration phase, the growth of Agrobacterium has to be inhibited, preferably the Agrobacterium cells have to be eliminated. This can be achieved, as well known in the art, by inclusion into the media of an antibiotic, toxic to Agrobacteria, such as but not limited to cefotaxime.

Regeneration of the transformed embryogenic callus into transgenic cotton plant lines, can performed according to methods which are well within the skills of the art, such as but not limited to the regeneration methods described in WO 98/15622.

In a preferred embodiment, small embryos are selected for germination and development into mature plants during the regeneration phase, preferably by growing the embryogenic callus in liquid medium on a gyratory shaker, and withholding for germination that fraction of the liquid suspension of embryogenic calli or somatic embryos which pass through a sieve, such as a tea-sieve.

A transgenic "cotton plant line" as used herein, consists of a group of transgenic cotton plants, originating from one transformed embryogenic callus piece, obtained during the regeneration process. In general, plants from one plant line are genetically identical, and originate from one transformation event, thus comprising the same transgenes integrated at the same genomic positions. However, individual plants from one plant line can originate from independent transformation events when using Agrobacterium-mediated DNA transfer, and may thus differ from one another. When transformation frequencies are expressed by the number of plant lines/100 initial embryogenic callus pieces, it may be that the actual transformation frequencies (transformation events/100 initial callus pieces) are even higher.

The methods of the invention are particularly suited for the transformation of all cotton plants from which embryogenic callus can be derived (both *Gossypium hirsutum* and *Gossypium barbadense*) particularly for Coker 312, Coker310, Coker 5Acala SJ-5, GSC25110, FiberMax 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA and plants with genotypes derived thereof.

The obtained transformed cotton plant can be used in a conventional breeding scheme to produce more transformed cotton plants with the same characteristics or to introduce the DNA fragment of interest into other varieties of the same or related cotton species, and methods further comprising such breeding activities are also included within the scope of the invention.

The following Examples describe the methods of the invention in detail. Unless stated otherwise in the Examples, all recombinant DNA techniques are carried out according to standard protocols as described in Sambrook et al. (1989) *Molecular Cloning: A Laboratory Manual,* Second Edition, Cold Spring Harbor Laboratory Press, NY and in Volumes 1 and 2 of Ausubel et al. (1994) *Current Protocols in Molecular Biology, Current Protocols,* USA Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

EXAMPLES

Example 1

Media, Plasmids and Bacterial Strains Used in the Examples
1.1 Media
Min A-glucose (MAG: Agrobacterium Growth Medium)
AB Medium (Agrobacterium Growth Medium)
1 liter AB medium contains 50 ml AB buffer, 50 ml AB salts, 5 g/l glucose and 12 g/l agar if appropriate.
Medium 100
Murashige & Skoog Salts+

30 g/l glucose 10 mg/l thiamine 100 mg/l inositol 1 mg/l nicotinic acid 1 mg/l pyridoxine 0.5 g/l MES buffer pH=5.8

Add 1.6 g/l gelrite and 0.75 g/l $MgCl_2.6H_2O$ whenever solid medium 100 is required
Medium 104
Murashige & Skoog Salts+

30 g/l glucose 10 mg/l thiamine 100 mg/l inositol 1 mg/l nicotinic acid 1 mg/l pyridoxine 1 g/l potassium nitrate 0.5 g/l MES buffer pH=5.8

Add 2.0 g/l gelrite and 0.94 g/l $MgCl_2.6H_2O$ whenever solid medium 104 is required
Medium 700

Stewards Macro Elements
Stewards Micro Elements
FeEDTA 0.7 ml/l of a stock solution containing 0.54 g $FeCl_3.6H_2O$ and 0.74 g $Na_2EDTA$ in 100 ml $H_2O$ sucrose: 20 g/l pH=6.8

Solidify the medium with 1 g/l gelrite+0.47 g/l $MgCl_2.6H_2O$ and 2.25 g/l agar
Medium 701

Same composition as medium 700 but with 30 g/l glucose solidify the medium with 20 g/l agar
Medium 702

Same composition as medium 700 but with 5 g/l sucrose solidify the medium with 1.5 g/l gelrite+0.71 g/l $MgCl_2.6H_2O$ and 5 g/l agar.
1.2 Plasmids and Bacterial Strains
*Agrobacterium tumefaciens* Strain A3311

A3311 is *A. tumefaciens* strain C58C1Rif$^R$ comprising the helper Ti-plasmid pEHA101 (Hood et al. 1986, J. of Bacteriology, 168: 1291–1301) and T-DNA vector pTHW136. Plasmid pTHW136 was constructed in the following way. An about 2.4 kb BamHI DNA fragment comprising the nos promoter-nptII-3'ocs cassette was inserted in pGSV5, yielding pGSV6. A HindIII fragment from p35SGUSINT comprising the CaMV35S promoter operably linked to a uidA gene containing a plant intron (Van Canneyt et al., 1990) was introduced into the HindIII site of pGSV6. The CaMV35S promoter can easily be replaced in this T-DNA vector by replacing the about 0.4 kb XbaI fragment. pGSV5 was derived from plasmid pGSC1700 (Comelissen and Vandewiele 1989, Nucl. Acids Res. 17, 833) but differs from the latter in that it does not contain a β-lactamase gene and that its T-DNA is characterized by the sequence of SEQ ID No 1.

*Agrobacterium tumefacients* Strains A3784

A3784 is *A. tumefaciens* strain C58C1RIF$^R$ comprising the helper Ti-plasmid pEHA101 (Hood et al. 1986) and T-DNA vector pTCO192. pTCO192 is similar to pGSV71 and differs from the latter only in the presence of a region homologous to the nptI gene of pEHA101, located outside of the T-DNA borders.

pGSV71 is a T-DNA vector derived from pGSC1700 (Cornelissen and Vandewiele 1989, Nucl. Acids Res. 17, 833) differing by the absence of the β-lactamase gene and the presence of the T-DNA characterized by the sequence of SEQ ID No. 2. pGVS71 comprises the selectable chimeric bar marker gene, operably linked to a CaMV35S promoter and the 3' end of the nopaline synthase gene.

*Agrobacterium tumefaciens* strain A3724

A3724 is *A. tumefaciens* strain C58C1Rif$^R$ comprising the helper Ti-plasmid pEHA101 (Hood et al. 1986) and T-DNA vector pTSVH9901. T-DNA vector pTSVH9901 is derived from the T-DNA vector pTSVH9901 is derived from the T-DNA cloning vector pGSV5, comprising between its border sequences a chimeric plant expressible bar gene, under control of a CaMV35S promoter and followed by a 3' end formation signal from a nopaline synthase gene. T-DNA vector pTSVH9901 also contains between its border sequences a chimeric plant expressible Cry9C gene, wherein the CRY9C encoding open reading frame is inserted between a CaMV35S promoter and 3" end region, and wherein a cab22L leader has been inserted in the untranslated mRNA encoding region. The T-DNA vector further comprises a region, homologous to the nptI gene of pEHA101, located outside of the T-DNA borders. pGSV5 was derived from plasmid pGSC1700 (Cornelissen and Vandewiele 1989, Nucl. Acids Res. 17, 833) but differs from the latter in that it does not contain a β-lactamase gene and that its T-DNA is characterized by the sequence of SEQ ID No 1.

*Agrobacterium tumefaciens* Strain A3727

A3311 is *A. tumefaciens* strain C58C1Rif$^R$ comprising the helper Ti-plasmid pEHA101 (Hood et al. 1986) and T-DNA vector pTSHV0203. T-DNA vector pTSHV0203 is based on the T-DNA cloning vector pGSV5 (WO 98/31822), comprising between its border sequences a chimeric plant expressible bar gene, under control of a CaMV35S promoter and followed by a 3' end formation signal from a nopaline synthase gene. T-DNA vector pTSHV0203 also contains between its border sequences a chimeric plant expressible Cry1Ab gene, wherein the CRY1Ab encoding open reading frame is inserted between a CaMV35S promoter and a 3' end region from the octopine synthase gene. The T-DNA further comprises a region homologous to the nptI gene of pEHA101, located outside of the T-DNA borders Example 2
Inclusion of a Plant Phenolic Compound Such as Acetosyringone During Cocultivation Allows Agrobacterium Mediated Transformation of Embryogenic Cotton Callus Embryogenic cotton callus was obtained in the following way: Cotton seeds of variety Coker 312 were disinfected using a 12% sodium hypochloride solution, and germinated individually in tubes containing a solution of gelrite 2/g/l H$_2$O and 0.94 g/l MgCl$_2$.6H$_2$O. The tubes were incubated in the dark at 27–28° C. After 10 to 14 days, seedlings are collected, the hypocotyls of the seedlings were cut in segments of about 1 cm and incubated on medium 104 (without plant hormones) at 28° C. under a regime of 16 hr light and 8 hr dark. Every three weeks, the segments were transferred to fresh medium, until embryogenic callus was formed (usually after about 9 weeks). This callus was removed from the explants and cultured further on medium 104.

Agrobacterium strain A 3311 cells were grown on AB medium or MAG medium, collected and resuspended in M104 liquid medium, pH 5.2 (either with or without 100 μM acetosyringone (AS)) or MAG medium at a density of about 1×10$^9$ CFU/ml. Small embryogenic cotton callus clumps were collected, washed in liquid medium 104 at pH 5.2, and immersed in the Agrobacterium suspension for about 20 minutes. The infected embryogenic calli were than transferred to solid medium 104, pH 5.2, supplemented with either 100 μM AS, 0.5 g/l casamino acids, 100 μM AS and 0.5 g/l casamino acids, or not supplemented at all, and incubated for cocultivation during 4 days in the dark at about 24° C.

After the cocultivation phase, the callus clumps were transferred to selective medium 104 supplemented with 50 mg/l kanamycin and 500mg/l Claforan.

At different time intervals after the cocultivation, samples of embryogenic callus were collected and subjected to a β-glucuronidase assay, using a chromogenic substrate as described by Jefferson et al. (1987; Plant Mol. Biol. Rep. 5: 387–405). The results of these tests are summarized in table 1, and are expressed as the percentage of calli expressing GUS-positive spots.

As a control, experiments were included using tobacco leaf discs co-cultivated with A3311, using mock-inoculated tobacco leaf discs or using mock-inoculated embryogenic cotton callus.

It is clear from the results that inclusion of acetosyringone is required during Agrobacterium mediated transformation of embryogenic callus, both for transient expression and after prolonged cultivation of the transformed calli.

Example 3
Agrobacterium Mediated Transformation of Cotton Using Embryogenic Callus Cotton embryogenic callus (EC) was generated as described in Example 2. Clumps of embryogenic callus were collected and washed in liquid medium 104 pH 5.2.

Agrobacterium strains A3784, A3724 and A3727 were grown for 3 to 4 days on AB medium pH 7.0, collected and resuspended at a density of approximately 1 to 5×109 cells/ml in liquid medium 104, pH 5.2 containing 100 μM acetosyringone.

Embryogenic callus clumps were immersed in the Agrobacterium suspension for maximum about 20 minutes, and transferred for cocultivation during 4 days in the dark at 24° C. on solid medium 104, p H5.2 supplemented with 100 μM acetosyringone.

After this cocultivation, the pieces of callus were transferred to a selective medium 104, pH 5.8, without acetosyringone or plant hormones, supplemented with 500 mg/l Claforan® (to inhibit the development of the Agrobacterium cells) and 5 mg/l phosphinotricin (PPT) (to select specifically for growth of transgenic calli).

Healthy looking pieces of embryogenic callus, actively growing, were transferred every 3 weeks to fresh selective medium 104.

Part of the callus (about 200 mg) was resuspended in 20 ml liquid medium 100, supplemented with 5 mg/l PPT in a 100 ml flask on a rotary shaker (100–120 rpm).

After two weeks culture in the liquid medium, large clumps were removed by passing the suspension through a tea-sieve. The fraction passed-through fraction of embryogenic suspension was left to settle for about 20 min, after which spent medium was removed and replaced by fresh medium 100.2 ml of this suspension of small embryo's were plated on solid medium 104, supplemented with 5 mg/l PPT and incubated at 28° C.

After about 2 weeks, developing embryos with a size between 4 and 10 mm were transferred to medium 701 and further incubated in the dark at 28° C . Smaller embryos were transferred to medium 104 overlaid with sterile filter paper (with or without 5 mg/L PPT) to allow increase in size, sufficient for transfer to medium 701.

After about 2 weeks, the embryos were transferred to medium 702 (with or without selective pressure) for germination, and incubated at 28° C., 16 hr light/8 hr dark.

Well developed plantlets (which may require 2 to 3 transfers on medium 702) were transferred to small containers containing M700. When these plantlets have developed two to three true leaves they were transferred to bigger containers with medium 700.

When the plants were about 10 cm in height, they were transferred to soil under greenhouse conditions.

Molecular analyses (Phosphinotricin acetylation assay, Southern hybridization, and ELISA to detect cry gene expression if appropriate) were performed on the callus level.

The results of these experiments are summarized in Table 2. Simultaneous Agrobacterium mediated transformation experiments of cotton cotyledons according to the methods known in the art, were performed for comparison.

What is claimed is:

1. A method for producing a transgenic cotton plant comprising the steps of:
   incubating Agrobacterium cells comprising a DNA fragment of interest operably linked to at least one T-DNA border, with a plant phenolic compound capable of inducing increased vir gene expression in said Agrobacterium cells;

co-cultivating solid cotton embryogenic callus cultivated on solid media with said Agrobacterium cells to generate embryogenic callus comprising a transformed cotton cell; and regenerating a transgenic cotton plant from said transformed cell;

wherein said incubating step occurs prior to or during said co-cultivation step.

2. A method for producing a transgenic cotton plant comprising the steps of:

co-cultivating solid cotton embryogenic callus cultivated on solid media with Agrobacterium cells, said Agrobacterium cells comprising a DNA fragment of interest operably linked to at least one T-DNA border, in the presence of a plant phenolic compound capable of inducing increased vir gene expression in said Agrobacterium cells, for a time sufficient to generate embryogenic callus comprising a transformed cotton cell; and regenerating a transgenic cotton plant from said transformed cell.

3. The method of claim 2, wherein said plant phenolic compound is present in a concentration range from about 50 $\mu$M to about 400 $\mu$M.

4. The method of claim 2, wherein said Agrobacterium cells are co-cultivated in the presence of said plant phenolic compound for a time period of about 3 to 4 days.

5. The method of claim 2, wherein said embryogenic callus is derived from a hypocotyl of a cotton seedling.

6. The method of claim 2, wherein said plant phenolic compound is acetosyringone, $\alpha$-hydroxy-acetosyringone, sinapinic acid, syringic acid, ferulic acid, catechol, p-hydroxybenzoic acid, $\beta$-resorcylic acid, protocatechuic acid, pyrrogallic acid, gallic acid or vanillin.

7. The method of claim 6, wherein said plant phenolic compound is acetosyringone.

8. The method of claim 2, wherein said Agrobacterium cells comprise helper Ti-plasmid pEHA101.

9. The method of claim 2, further comprising the step of crossing said transgenic cotton plant with another cotton plant.

10. A process for producing a transgenic cotton plant comprising:

co-cultivating solid cotton embryogenic callus cultivated on solid media, wherein said cotton embryogenic callus has not been generated from a cotton explant comprising transformed cells, with Agrobacterium cells in the presence of a plant phenolic compound capable of inducing increased vir gene expression in said Agrobacterium cells; said Agrobacterium cells comprising a DNA fragment of interest operably linked to at least one T-DNA border; wherein said Agrobacterium cells are cocultivated with said cotton embryogenic callus for a time sufficient to generate embryogenic callus comprising a transformed cotton cell; and regenerating a transgenic cotton plant from said transformed cell.

* * * * *